(12) United States Patent
Nikolaevich et al.

(10) Patent No.: US 6,322,557 B1
(45) Date of Patent: Nov. 27, 2001

(54) DEVICE FOR REMOVING CATARACTS (76) Inventors: Fedorov Svyatoslav Nikolaevich, pereulok Dostoevskogo, d. 1/21, kv. 32; Kopaeva Valentina Grigorievna, Dmitrovskoe shosse, d. 59, kv. 169, both of Moscow; Belikov Andrei Vyacheslavovich, prospekt Narodnogo opolchenia, d. 141, kv. 86; Erofeev Andrei Viktorovich, ulitsa Budapeshtskaya, d. 74, kv. 27, both of Sankt-Peterburg; Andreev Jury Vladislavovich, Beskudinovsky bulvar, d. 59A, kv. 802, Moscow, all of (RU)

( * ) Notice: Subject to any disclaimer, the term of this patent is extended or adjusted under 35 U.S.C. 154(b) by 0 days.

(21) Appl. No.: 09/209,402

(22) Filed: Dec. 10, 1998

(30) Foreign Application Priority Data

Dec. 10, 1997 (RU) ................................. 97120606

(51) Int. Cl.[7] .................................................. A61B 18/18
(52) U.S. Cl. ...................... 606/6; 606/4; 606/10; 606/13; 606/127; 607/89
(58) Field of Search .............................. 606/4–6, 10–12; 607/88, 89

(56) References Cited

U.S. PATENT DOCUMENTS

| | | | |
|---|---|---|---|
| 4,825,865 | * 5/1989 | Zelman | 128/303.1 |
| 5,057,098 | * 10/1991 | Zelman | 606/6 |
| 5,139,504 | 8/1992 | Zelman . | |
| 5,257,988 | * 11/1993 | L'Esperance, Jr. | 606/6 |
| 5,324,282 | * 6/1994 | Dodick | 606/15 |
| 5,370,641 | * 12/1994 | O'Donnell, Jr. | 606/4 |
| 5,445,637 | * 8/1995 | Bretton | 606/41 |
| 5,733,276 | * 3/1998 | Belkin | 606/6 |
| 5,843,071 | * 12/1998 | Bath | 606/6 |
| 5,957,914 | * 9/1999 | Cook et al. | 606/6 |

* cited by examiner

*Primary Examiner*—Linda C. M. Dvorak
*Assistant Examiner*—Ahmed M. Farah
(74) *Attorney, Agent, or Firm*—Ostrolenk, Faber, Gerb & Soffen, LLP (57) ABSTRACT

A device for removing cataracts comprises a source of pulse laser radiation, including a laser tip, and means for irrigation-aspiration provided with a tip. The tips serve for insertion into an eye cavity through first and second cuts and have a working part serving for placement in the anterior section of the eye when a cataract-changed lens is being removed. The laser tip is placed at an angle which is within the range of from 1 to 180 degrees relative to the tip of the means for irrigation-aspiration. Means for concentrating an acoustic wave is made in the form of at least one hollow body, the walls of which are made of a material, the light absorption factor of which at the wavelength of laser radiation is within the range of from 0.001 cm$^{-1}$ to 10 000 cm$^{-1}$, and the ratio of the length of which to the internal diameter is within the range of from 1 to 100. The means for concentrating the acoustic wave on the cataract-changed lens of an eye is placed coaxially either with the laser tip or with the tip for irrigation-aspiration or on an additional tip.

12 Claims, 8 Drawing Sheets

DEVICE FOR REMOVING CATARACTS

FIELD OF THE INVENTION

The present invention relates to medicine, and more exactly—to devices for removing cataracts.

The device may be used to remove a cataract of any etiology, in particular, very dense cataracts.

BACKGROUND OF THE INVENTION

A device is known for removing cataracts which comprises a source of laser radiation with a laser tip and means for irrigation-aspiration provided with a wedge-shaped tip, wherein the working parts of said tips are placed in the front section of the eye when a cataract-changed lens is being removed (see, e.g., U.S. Pat. No. 5,139,504).

The following steps are carried out in order to remove a cataract. The focus of a solid-body niobium laser Nd:YAG with a wavelength of 1.06 nm is directed transcorneally to the middle layers of the lens by adjusting the sharpness of a surgical microscope to the irradiated area. A light guide conducting the laser radiation is mounted in the drawtube. The generation of 20–30 pulses of laser radiation is effected with the power of each pulse being 0.2–0.5 mW/cm kV, length–10 ns, radiation power 5–10 J, size of the light spot–50 micrometers. Right after termination of the laser action, a step-like three-profile cut is formed and capsulotomy is carried out, the tip, phacoemulsifier, is entered into the eye cavity, aspiration and generation of ultrasound are turned on within the limits of 10–30% of the total power of the apparatus.

Preliminary laser action results in mechanical destruction of the links between fibers of the lens due to the formation of a plasma cloud be having the capability of expanding at supersonic speed, which weakens the stability of the lens substance to aspiration and weakens the resistivity of the lens to ultrasound oscillations, reduces the threshold values of the ultrasound power, and brings to a minimum the negative effect of the influence of ultrasound on the eyeball.

This device does not make it possible to carry out full-fledged fragmentation of the lens through the whole thickness thereof, since upon action of radiation on the substance of the lens opacities are produced which impair visual monitoring of the course of the operation and make it difficult to apply subsequent laser actions. The process of supplying a large number of laser pulses is made more difficult in the presence of dense cataracts, since there is no reflection from the fundus of the eye and there is no possibility of determining the structure of the lens in an optical cut. The device does not make it possible to carry out full laser cleavage of the lens, and therefore it is not possible to talk about a substantial reduction in the resistivity of the lens substance to aspiration and ultrasonic oscillations.

Laser irradiation at a wavelength of 1.06 nm has a traumatic effect on eye tissues, since in that case a photo-ionization regime is mainly generated, this regime consisting of the formation of a plasma cloud which upon expanding generates a powerful impact wave which deforms the surrounding tissues.

When two types of destructive action are simultaneously used on the lens, the drawbacks of ultrasound action—cavitation which is difficult to monitor and is traumatic for eye tissues, are added to the drawbacks of laser action. Wherein the energetic parameters of the laser action and ultrasound oscillations increase as the density of a cataract increases, and therefore the device may be suitable for removing soft uncomplicated cataracts.

A drawback of this device is that it is not possible to work with solid lenticular masses, the operation is lengthy and there is increased traumatism related to non-optimum action of the laser radiation.

A device is known for removing cataracts which comprises a source of pulse laser radiation with a laser tip and means for irrigation-aspiration provided with a tip, wherein the working parts of said tips are placed in the anterior section of the eye during removal of a cataract-changed lens (see, e.g., a prospectus of the Premier Laser Systems Inc. firm, 5, 1996).

A laser with a wavelength of 2.94 micrometers is used in the aforesaid device, wherein the laser light guide lies inside the aspiration channel. The latter is formed by a metal tube with an internal diameter of 0.8 mm. The irrigation channel is formed due to a gap between a silicone cap placed on the metal tube. The magnitude of the gap is not more than 0.2 mm. In order to create a vacuum, a vacuum pump is used which is connected to the device by means of silicone hoses.

When turned on, the laser radiation along the light guide falls on the surface of the lens. During one pulse a local defect is formed in the lens with a depth of 3–4 micrometers and width of 400 micrometers. The laser generates from 10 to 40 pulses per second. When the substance of the lens is partially evaporated, a finely dispersed suspension is partially formed in the liquid medium and is sucked out along the aspiration channel. A physiological solution supplied along the irrigation channel is used as the liquid. The amount of liquid being fed corresponds to the amount of liquid being sucked out.

Since the laser pulses have a limited depth of penetration into the tissue of the lens, quite a long period of time, about 10–12 minutes is required for the complete destruction of the lens. This creates serious difficulties during the step of forming a crater in the lens, since it is necessary to forcefully press the tip against the surface of the lens. This creates the threat of disruption of the suspensory ligaments.

There is the problem of evacuation of the destroyed lens mass from the cavity of the eye. Laser pulses are transformed into acoustic oscillations. The direction of the acoustic oscillations is in the direction opposite to the direction of evacuation of liquid from the cavity of the eye, since laser pulses counteract suction of the lens substance into the aspiration channel. The width of the aspiration channel is small, not more than 0.2 mm. The suspension of destroyed lens substance may adhere into larger conglomerates which block the aspiration channel. Aspiration stops and it becomes impossible to continue the operation.

During fragmentation of the lens substance, the laser tip should be positioned at the level of the edge of the aspirational aperture, otherwise radiation will not reach the lens, and it is not possible to destroy the lens substance sucked against the aspiration aperture due to the fact that the divergence of the laser beam is small. Quite often there is complete blockage of the aspiration channel with undestroyed lens substance. A disbalance between the supplied and removed liquid results in a collapse of the anterior eye chamber, unstable depth of the anterior chamber, amoeboid movement of the iris, narrowing of the pupil, and disturbance of visual examination of the surgery field.

All of this results in an increase in the length of the operation which in turn increases the consumption of irrigation liquid and the possibility of traumatism, an increase in the probability of injury to the iris, the rear capsule and cornea at the moment of manipulation with the core. An increase of the temperature in the front chamber of the eye may also occur, since at the moment of blockage of the aspiration channel, liquid is not fed into the eye, and it is in particular the liquid that performs the function of removing the thermal energy. Thermal damage is especially dangerous for the cornea, since it results in irreversible changes in the corneal endothelium and subsequently to distrophy of the cornea.

SUMMARY OF THE INVENTION

The object of the present invention is to create a device for removing cataracts of any etiology, in particular very dense cataracts, in which the positioning of a laser tip at an angle to a tip of a means for irrigation-aspiration and the use of a means for concentrating an acoustic wave induced by a pulse laser radiation impinging on the lens of an eye, positioned coaxially with the tip for irrigation-aspiration and having smooth walls, and also the use of means for converting laser radiation, makes it possible to effect removal of a cataract having a high degree of density using the effect of additional crushing of the lens masses inside or outside of an aspirational channel, and avoid blockage of the aspiration channel, reduce traumatism of the operation, reduce consumption of irrigation liquid and the length of the operation, and also avoid overheating of the eye while the operation is being carried out.

These objects are achieved in a device for removing cataracts comprising a source of pulse laser radiation with a laser tip and means for irrigation-aspiration provided with a tip, wherein the working parts of the aforesaid tips are placed in the anterior section of the eye during removal of a cataract-changed lens, in that in accordance with the invention, the aforesaid tips serve for insertion into the cavity of an eye through two insulated cuts, wherein the laser tip is placed at an angle of from 1 to 180 degrees relative to the tip of the means for irrigation-aspiration, and the device further comprises means for concentrating on a cataract-changed lens of an eye or directly adjacent thereto an acoustic wave induced by pulse laser radiation impinging on the lens of an eye, the means for concentrating being made in the form of at least one hollow body, walls of which are made of a material, the light absorption factor of which at the wavelength of laser radiation is within the range of from 0.001 to 10 000 cm, and the ratio of the length of which to its inner diameter within the range of from 1 to 100, wherein the means for concentrating the acoustic wave on a cataract-changed lens of the eye is placed coaxially with the tip for irrigation-aspiration.

It is advisable that material selected from the group consisting of fluorite, sapphire, quartz, phosphate glass, be used as the material, the light absorption factor of which at the wavelength of laser radiation is within the range of from 0.001 cm to 10 000 cm.

It is useful that a hollow rod having a circular, elliptical or rectangular shape in cross section be used as the hollow body.

The stated objects are also achieved in a device for removing cataracts comprising a source of pulse laser radiation with a laser tip and means for irrigation-aspiration provided with a tip, wherein the working parts of the aforesaid tips are placed in the anterior section of the eye during removal of a cataract-changed lens, in that in accordance with the invention, the aforesaid tips serve for insertion into the cavity of an eye through two insulated cuts, wherein the laser tip is placed at an angle of from 1 to 180 degrees relative to the tip of the means for irrigation-aspiration, and the device further comprises means for concentrating on a cataract-changed lens of an eye or directly adjacent thereto an acoustic wave induced by pulse laser radiation impinging on the lens of an eye, the means for concentrating being made in the form of at least one hollow body, walls of which are made of material, the light absorption factor of which at wavelength of laser radiation is within the range from 0.001 to 10 000 cm$^{-1}$, and the ratio of the length of which to its inner diameter is within the range of from 1 to 100, wherein the means for concentrating the acoustic wave on a cataract-changed lens of the eye is placed coaxially with the laser tip.

It is advisable that the device further comprise means for changing the wave front of the acoustic wave and concentrating on a cataract-changed lens of the eye the acoustic wave induced by pulse laser radiation impinging on the lens of an eye, the means for changing being made in the form of a lens or body of cylindrical shape with a variable index of refraction and positioned on the distal end of the working part of the laser tip.

The stated objects are also achieved in a device for removing cataracts comprising a source of pulse laser radiation with a laser tip and means for irrigation-aspiration provided with a tip, wherein the working pars of the aforesaid tips are placed in the anterior section of the eye during removal of a cataract-changed lens, in that in accordance with the invention, the aforesaid tips serve for insertion into the cavity of an eye through two insulated cuts, wherein the laser tip is placed at an angle of from 1 to 180 degrees relative to the tip of the means for irrigation-aspiration, and the device further comprises means for concentrating on a cataract-changed lens of an eye or directly adjacent thereto an acoustic wave induced by pulse laser radiation impinging on the lens of an eye, the means for concentrating being made in the form of at least one hollow body, walls of which are made of material, the light absorption factor of which at the wavelength of laser radiation is within the range of from 0.001 to 10 000 cm$^{-1}$, and the ratio of the length of which to its inner diameter is within the range of from 1 to 100, wherein the device also comprises an additional tip which is placed in an additional aperture in the anterior section of the eye during removal of a cataract-changed lens at an angle to the tip for irrigation-aspiration which is within the range of from 1 to 180 degrees, and the means for concentrating an acoustic wave on the cataract-changed lens of the eye is placed in the additional tip.

It is advisable that the device comprise a means for converting at least a ¼ part of the laser radiation into an acoustic wave, positioned in the path of the laser beam and made of a material, the light absorption factor of which at the wavelength of laser radiation is greater than the light absorption factor at the wavelength of laser radiation of the material of the means for concentrating, wherein the means for converting be made in the form of a solid body or film or particle and be placed on a tip selected from the group consisting of the laser tip, the irrigation-aspiration tip and the additional tip, and also on the means for concentrating or in the body of the means for concentrating.

It is useful that the means for converting be made from a material selected from the group consisting of silver, gold, platinum, aluminum, carbon, and titanium oxide.

It is advantageous that a layer of material, the acoustic resistance of which is less than 100 Pa·s/m$^3$, be placed between the means for concentrating and the means for converting.

It is advisable that the wavelength of the source of laser radiation be within the range of from 1.06 to 2.94 micrometers.

It is useful that the device further comprise a modulator for converting the time structure of the laser pulse so that the modulation frequency of the laser pulse be equal to or a multiple of the resonance frequency of the means for concentrating the acoustic wave.

It is advantageous that the roughness factor (Rz) of the inner surface of the irrigation-aspiration tip be less than 0.05.

It is advisable that the device comprise a means for preventing the sucking of the rear wall of the crystalline capsule towards the aspiration channel, this means being made in the form of a scapula of polymeric material, which is fixed on the working part of the irrigation-aspiration tip.

The proposed device for removing cataracts makes it possible to effect removal of cataracts having a high degree of density, using the effect of additionally crushing the lens masses inside or outside the aspiration channel, wherein it is possible to avoid blockage of the aspiration channel, which substantially reduces the traumatism of an operation. It becomes possible to reduce the consumption of irrigation liquid and the length of the operation, and also to avoid overheating of the eye while an operation is being carried out.

DESCRIPTION OF THE DRAWING

Further the invention is explained by a description of concrete embodiments of its realization with reference to the accompanying drawings in which.

DETAILED DESCRIPTION OF THE PREFERRED EMBODIMENTS

The device for removing cataracts comprises a source 1 (FIG. 1) of pulse laser radiation with a laser tip 2 and means 3 for irrigation-aspiration for evacuating the lens destruction products, the means 3 being provided with a tip 4. The working portions of the aforesaid tips 2, 4 are placed in the anterior section 5 of the eye 6 when a cataract-changed lens 7 is being removed.

Figure 1:
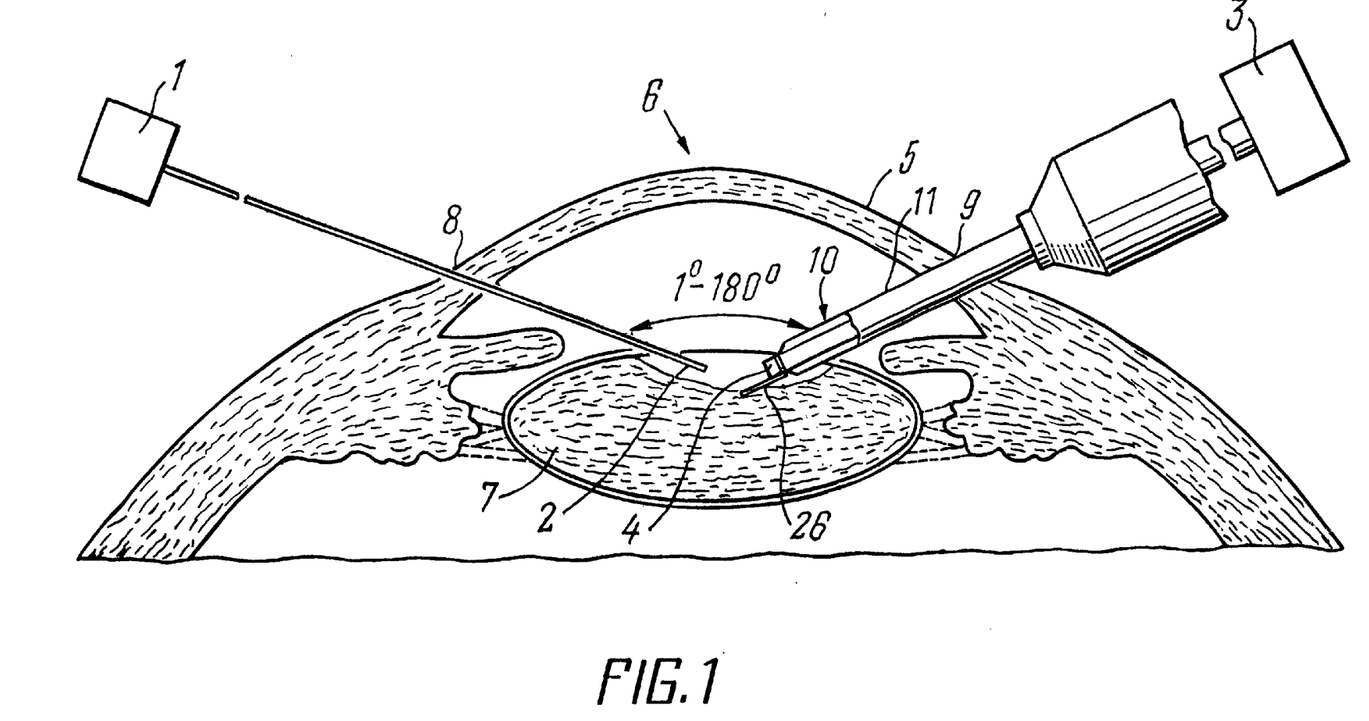
FIG. 1 shows the diagram of a device for removing cataracts, an embodiment wherein the means for concentrating an acoustic wave on a cataract-changed lens of an eye is placed on a tip for irrigation-aspiration, in accordance with the invention.

The tips 2, 4 are entered in the cavity of an eye 6 through two insulated cuts 8, 9 respectively, wherein the laser tip 2 may be placed at an angle of from 1 to 180 degrees relative to the tip 4 of the means for irrigation-aspiration. In the embodiment being described the aforesaid angle is 90 degrees angular.

The device additionally comprises a means 10 for concentrating an acoustic wave on a cataract-changed lens of the eye or directly adjacent thereto, the acoustic wave being induced by pulse laser radiation impinging on the lens 7 of the eye, the means 10 being made in the form of at least one hollow body. In the embodiment being described, the aforesaid means 10 is a cylinder 11, the walls of which are made of a material, the light absorption factor of which at the wavelength of laser radiation is within the range of from 0.001 cm to 10 000 cm. Wherein, the ratio of the length of the cylinder 11 to its inner diameter is within the range of from 1 to 100. The cylinder 11 (FIG. 1) is placed coaxially with respect to the tip 4 for irrigation-aspiration inside the working part of the tip 4.

A material selected from the group consisting of fluorite, sapphire, quartz, and phosphate glass is used as the material from which the cylinder 11, the light absorption factor of which at the wavelength of laser radiation is within the range of from 0.001 $cm^{-1}$ to 10 000 $cm^{-1}$, is made.

Figure 2A:
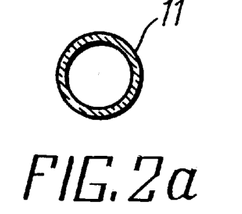
FIG. 2 shows views of a section of the means for concentrating, in accordance with the invention.
Figure 2B:
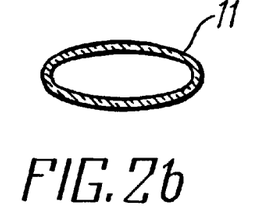
Figure 2C:
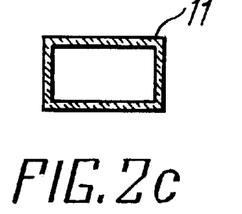

A rod having a cross section of circular (FIG. 2a), elliptical (FIG. 2b) or rectangular (FIG. 2c) shape may be used as the hollow body.

Figure 3:
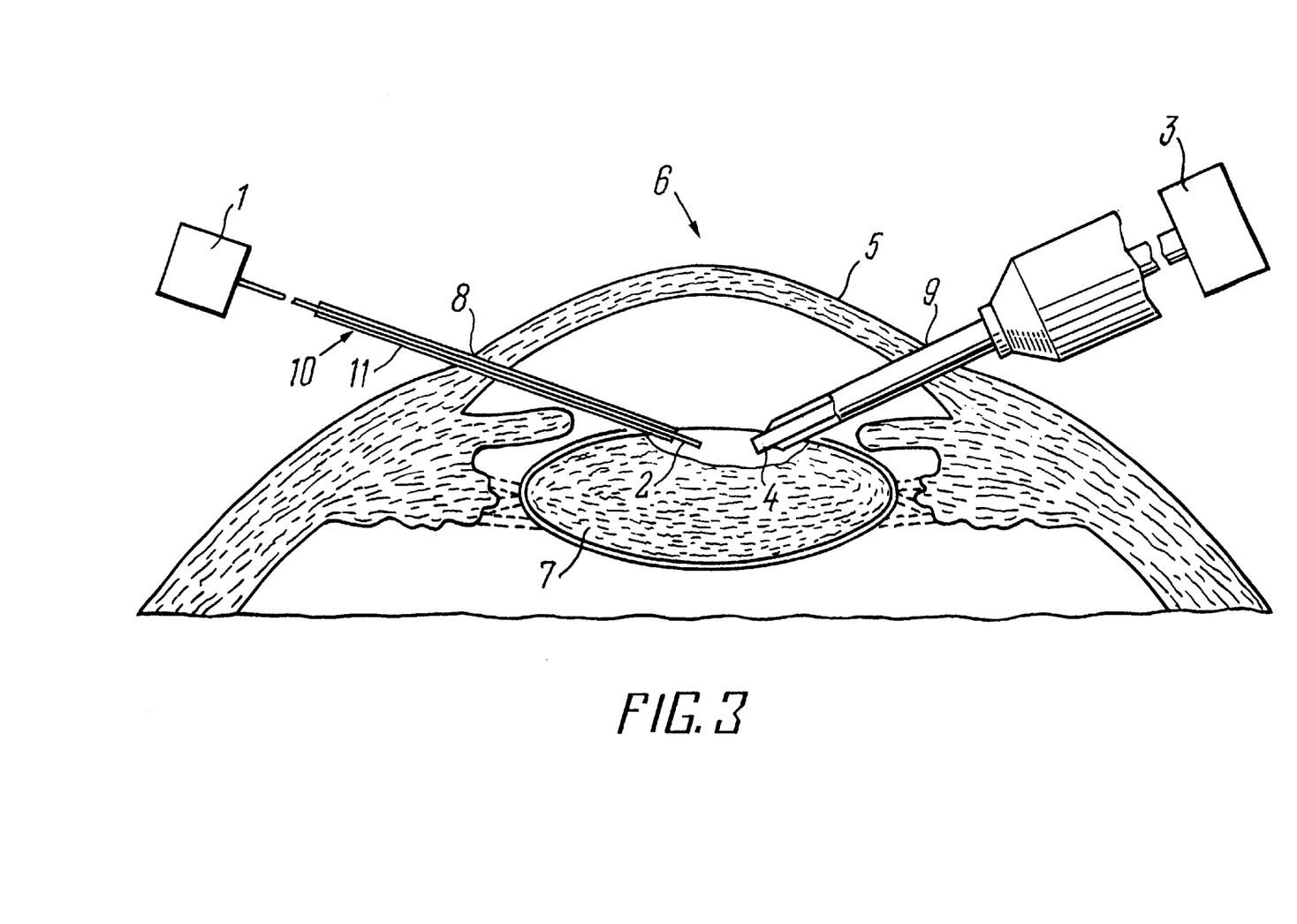
FIG. 3 shows a diagram of a device for removing cataracts, an embodiment wherein the means for concentrating an acoustic wave on a cataract-changed lens of an eye is placed on a laser tip, in accordance with the invention.

An alternative embodiment of the device for removing cataracts is possible wherein the means 10 for concentrating an acoustic wave on a cataract-changed lens of an eye is made in a manner similar to that described above, but is placed coaxially with respect to the laser tip 2 (FIG. 3).

Figure 4A:
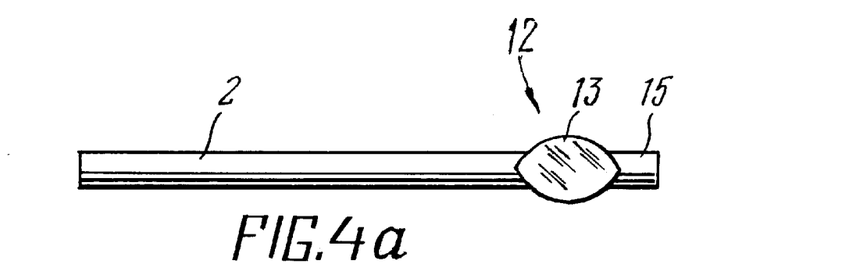
FIG. 4 shows a means for changing the wave front of the acoustic wave and for concentrating an acoustic wave induced by pulse laser radiation on a cataract-changed lens of an eye, in accordance with the invention.
Figure 4B:
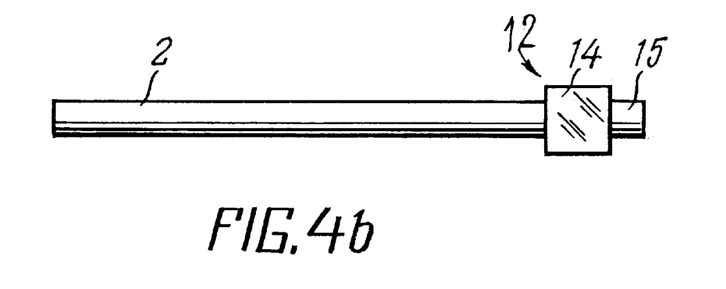

The device additionally comprises a means 12 (FIG. 4) for changing the wave front of the acoustic wave and concentrating an acoustic wave on a cataract-changed lens of an eye, the acoustic wave being induced by pulse laser radiation impinging on the lens 7 of an eye. The means 12 is made in the form of a lens 13 (FIG. 4a) or a body of cylindrical shape 14 (FIG. 4b), which have a variable index of refraction. The means 12 is placed on a distal end 15 of the working part of the laser tip 2.

Figure 5:
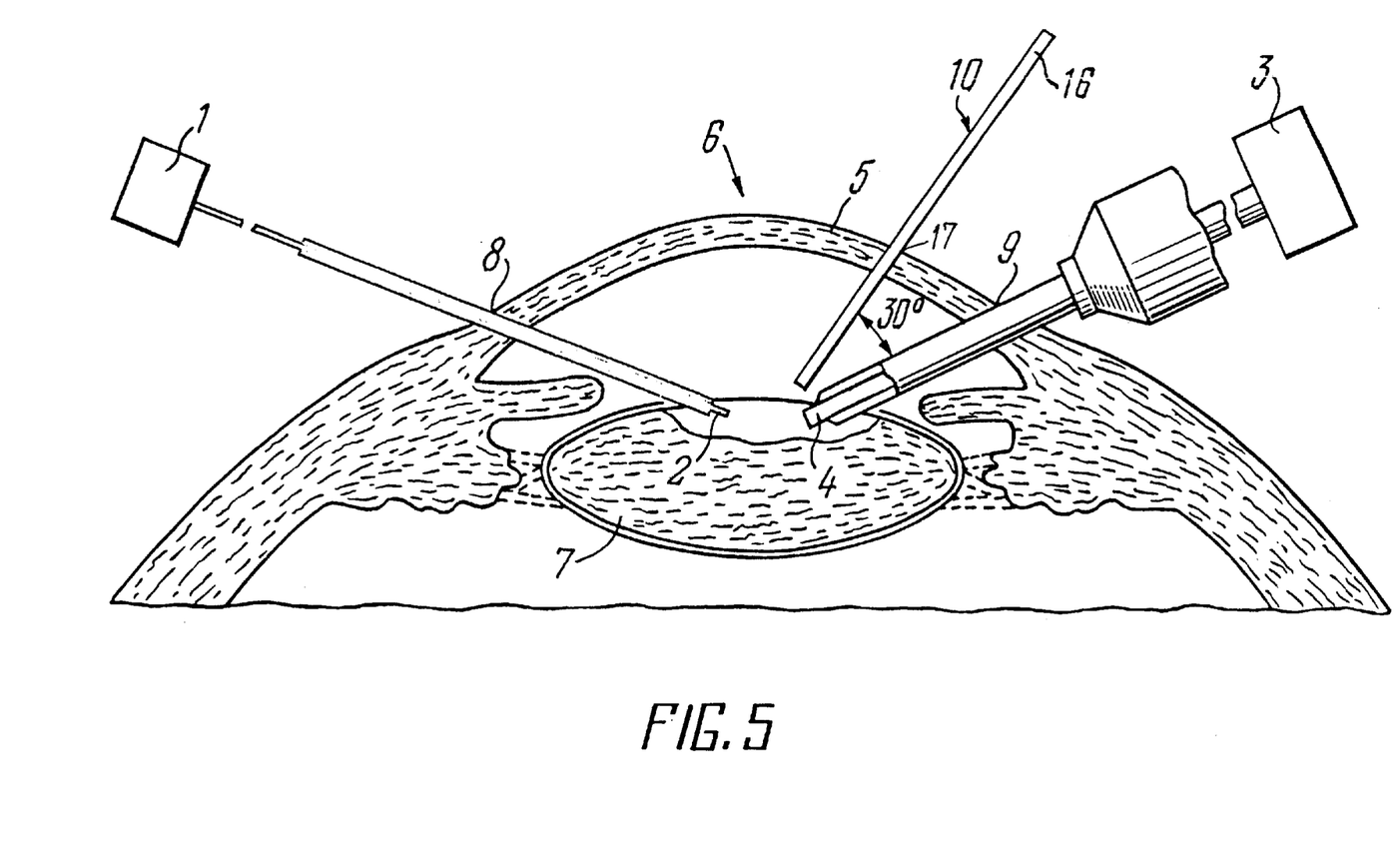
FIG. 5 shows a diagram of a device for removing cataracts, an embodiment wherein the means for concentrating an acoustic wave on a cataract-changed lens of an eye is placed on an additional tip, in accordance with the invention.

One more embodiment of the device for removing cataracts is possible, wherein the device comprises an additional tip 16 (FIG. 5), which is placed in an additional aperture 17 in the anterior section 5 of the eye 6 at an angle to the tip 4 for irrigation-aspiration, the angle being within the range of from 1 to 178 degrees. In the embodiment being described this angle is equal to 30 degrees. The means 10 for concentrating an acoustic wave on the cataract-changed lens of the eye is placed in the additional tip 16.

The device also comprises a means 18 for converting at least a ¼ part of the laser radiation into an acoustic wave, the means 18 being placed in the path of the laser beam. The means 18 is made of a material, the light absorption factor of which at the wavelength of the laser radiation is greater than the light absorption factor at the wavelength of laser radiation of the material of the means 10 for concentrating. The means 18 for converting may be made of a material selected from the group consisting of silver, gold, platinum, aluminum, carbon, and titanium oxide.

The aforesaid means 18 for converting is made in the form of a solid body, or film or particles, and may be placed on a tip selected from the group consisting of the laser tip 2, irrigation-aspiration tip 4 and additional tip 16, and also on the means 10 for concentrating or in the body of the means 10 for concentrating.

Figure 6:
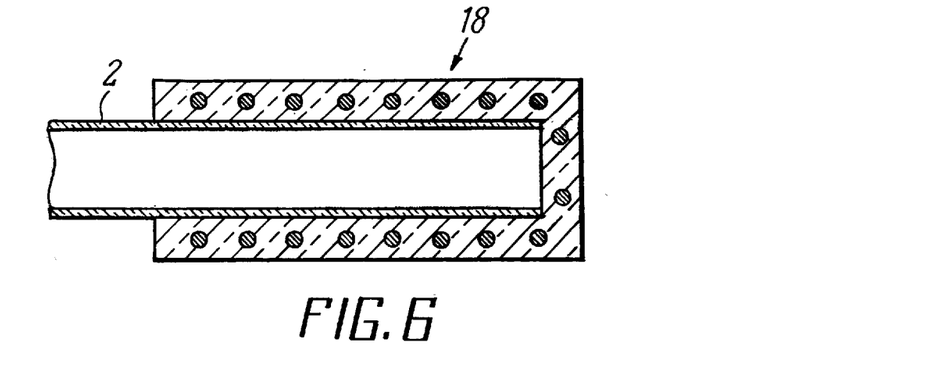
FIG. 6 shows a means for converting laser radiation into an acoustic wave, the means being placed on a laser tip, in accordance with the invention.

FIG. 6 shows an embodiment wherein the means 18 is placed on the working part of the laser tip 2 and is a plug of glass with inclusions of silver or gold, which is set on the laser tip 2.

Figure 7:
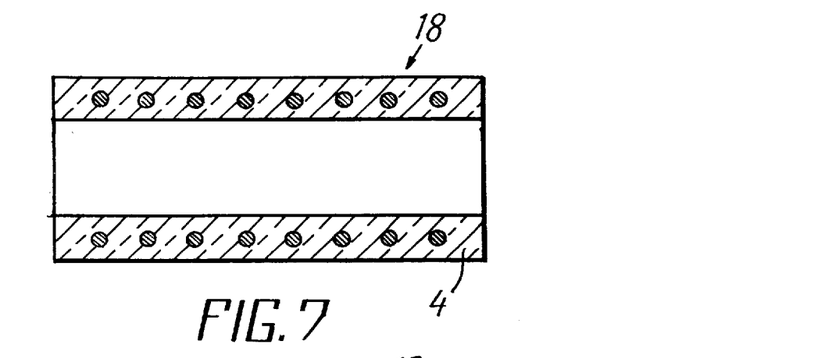
FIG. 7 shows a means for converting laser radiation into an acoustic wave, the means being placed on an irrigation-aspiration tip, in accordance with the invention.

FIG. 7 shows an embodiment wherein the means 18 is made integral with the working part of the irrigation-aspiration tip 4 and is a glass tube with inclusions of platinum or aluminum or titanium oxide.

Figure 8:
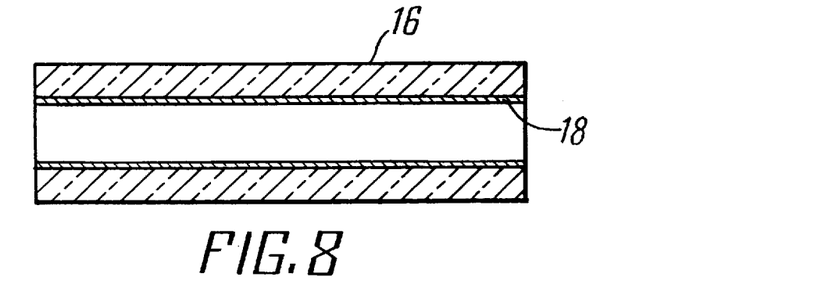
FIG. 8 shows a means for converting laser radiation into an acoustic wave, the means being placed on an additional tip, in accordance with the invention.

FIG. 8 shows an embodiment wherein the means 18 is made in the form of a solid layer of material selected from the group consisting of silver, gold, aluminum, carbon, and titanium oxide, placed on the inner surface of the additional tip 16. A variant is possible (not shown in the drawing), wherein the solid layer is placed on the outer surface of the tip 16.

Figure 9:
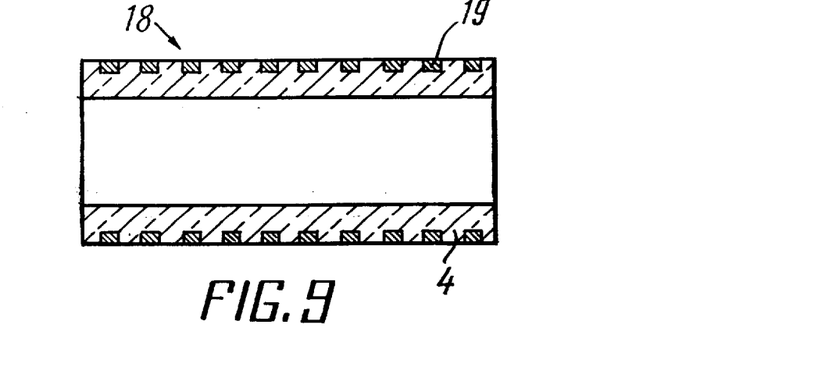
FIG. 9 shows a means for converting laser radiation in an acoustic wave in the form of recesses, the means being placed on an irrigation-aspiration tip, in accordance with the invention.

One more embodiment is possible, wherein the means 18 is made in the form of a layer placed on the outer surface of the irrigation-aspiration tip (not shown in a drawing), or the means 18 (FIG. 9) may be made integral with the irrigation-aspiration tip 4 wherein, recesses 19, filled, for example, with titanium oxide powder, are made on the outer surface of the irrigation-aspiration tip 4.

One more embodiment is possible, wherein the means 10 for concentrating and the means 18 for converting are simultaneously placed on the irrigation-aspiration tip 4 (FIG. 10), a layer 20 of a material, the acoustic resistance of which is less than 100 Pa·s/m$^3$, for example, a layer of glass, is placed between the means 10 and the means 18. This layer is necessary so that the acoustic wave is effectively passed to the means 10 for concentrating.

Figure 11:
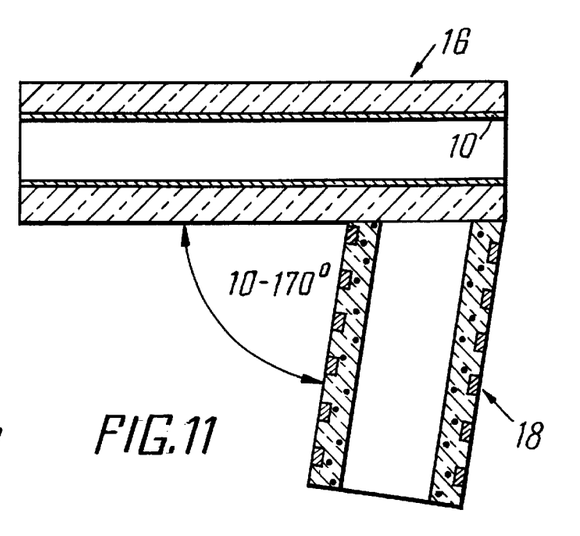
FIG. 11 shows means for converting laser radiation into an acoustic wave in the form of recesses and inclusions and means for concentrating, these means being placed on an additional tip, in accordance with the invention.

The aforesaid means 10 and 18 may be placed on the additional tip 16 (FIG. 11) so that the means 10 for concentrating is placed on the inner surface of the additional tip 16, while the means 18 for converting is fixed on the outer side of the additional tip 16 directly adjacent to its end at an angle of from 10 to 170 degrees.

The wavelength of the source 1 of laser radiation is within the range of from 1.06 to 2.94 micrometers and is selected on the basis of the absorption factor of tissues of a cataract-changed lens and minimum damage to the surrounding tissues.

The device additionally comprises a modulator (not shown in a drawing) for converting the time structure of the laser pulse so that the modulation frequency of the laser pulse is equal to or a multiple of the resonance frequency of the means for concentrating the acoustic wave. Modulation of the laser radiation makes it possible to more effectively convert the laser radiation in an acoustic wave, since with an increase of the depth of modulation the part provided by the acoustic power increases, and the resonance makes it possible to most effectively transmit the energy of the acoustic wave to the biotissue.

The roughness factor (Rz) of the inner surface of the irrigation-aspiration tip 4 is less than 0.05.

The device for removing cataracts works in the following manner.

The tip 4 of the means 3 for irrigation-aspiration is entered into the anterior chamber 5 (FIG. 1) of the eye 6 through a 2 mm main cut 9. The means 10 for concentrating an acoustic wave and the means 18 for converting (not shown) are placed in the working part of the tip 4.

The working part of the laser tip 2 is entered through the additional cut 8 at the limbus at an angle of 90 degrees to the main cut 9 in the anterior chamber 5 of the eye 6.

The tip 4 (FIG. 12) comprises two hollow tubes 21, 22. The outer tube 22 serves to create an irrigation channel for supplying irrigation liquid into the cavity of the eye through apertures 23. The inner tube 21 has walls which are transparent for the length of the wave generated by the laser and comprises a means 18 for converting laser radiation made in the form of inclusions of gold and means 10 for concentrating made in the form of a film of fluorite. The channel 19 of the tube 21 serves as the channel through which aspiration is carried out by means of a vacuum created by a vacuum pump (not shown).

Figures 10, 12:
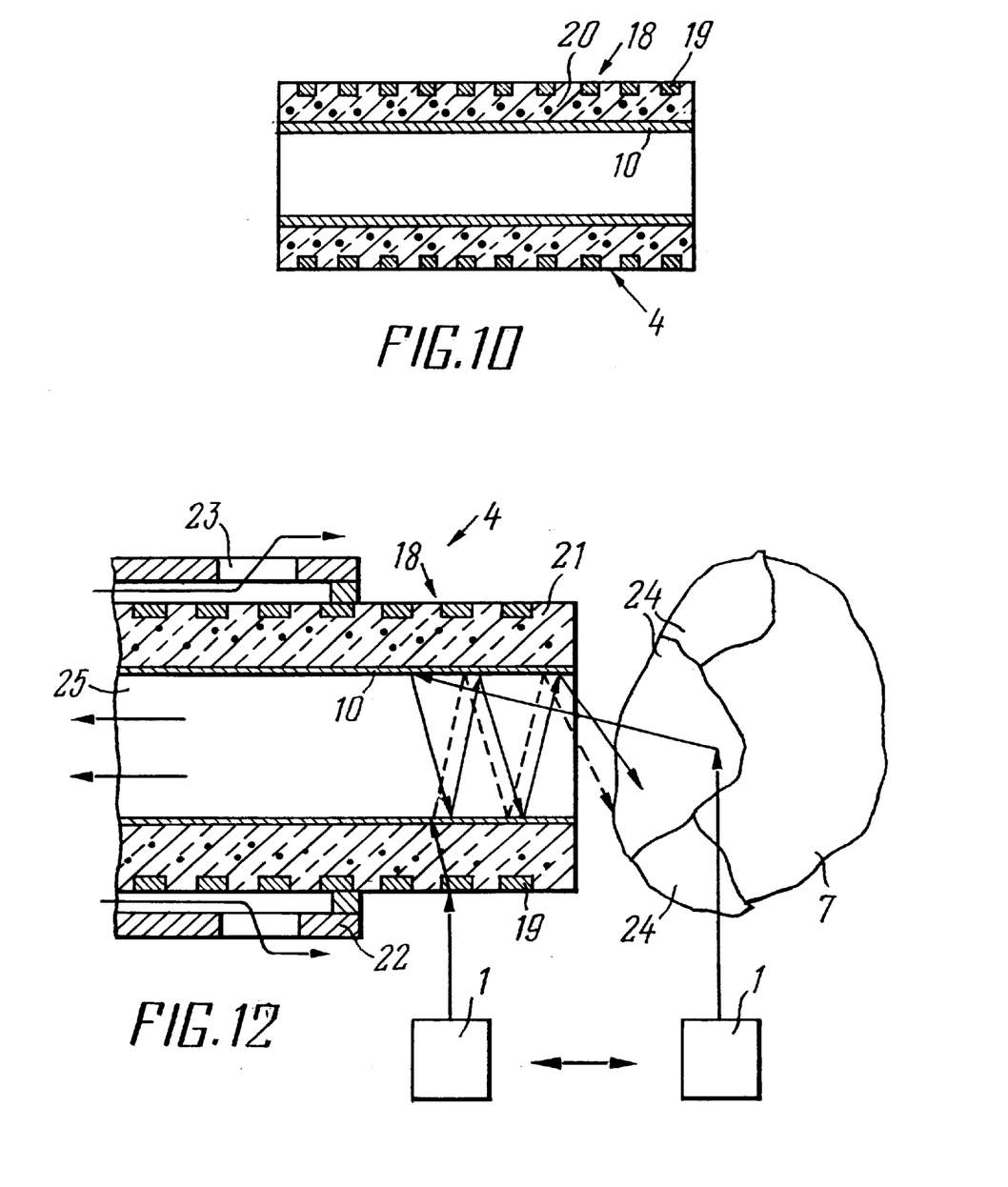
FIG. 10 shows a means for converting laser radiation into an acoustic wave in the form of recesses and inclusions and means for concentrating, these means being placed on an irrigation-aspiration tip, in accordance with the invention.
FIG. 12 shows the principle of operation of the device for removing a cataract, the initial stage of the surgical operation, in accordance with the invention.

The means 3 for irrigation-aspiration is turned on. The tip 4 is arranged so that the end of the inner tube 21 would be at a distance of approximately 1–2 mm from the surface of the lens 7. The source 1 of pulse laser radiation is turned on. The laser radiation is directed to the surface of the lens 7. The working end of the optical fiber is positioned at a distance of about 1 mm from the surface of the lens 7.

Laser radiation upon interaction with the substance of the lens 7 is converted into an acoustic wave (shown by the solid line with arrows in FIG. 12). The acoustic wave spreads in the anterior chamber 5 of the eye and gets into the hollow tube 21 where the means 10 for concentrating and the means 18 for converting are located. Multiple amplification of the acoustic wave takes place in the hollow tube 21 due to multiple reflection of the acoustic wave from the walls of the means 10 for concentrating. Then the amplified wave is directed to the surface of the lens 7 and breaks it up causing fragmentation of the lens fibrils.

Movement of the laser tip 2 over the surface of the lens 7 is effected, which results in expansion of the defect and the formation of a crater in the lens 7. Movement of the laser tip 2 is effected in the direction of the tip 4 and it is positioned above the surface of the tube 21. Laser radiation falls on the surface of the means 18 for converting and is transformed into acoustic oscillations which are transmitted to the inner surface of the tube to the means 10 for concentrating and are amplified a multiple number of times by the means 10 (shown in FIG. 12 by the dashed line). Amplified acoustic oscillations are directed to the surface of the lens 7, causing further fragmentation of the lens substance, which results in final division of the lens 7 into several separate lens segments 24.

Figure 13:
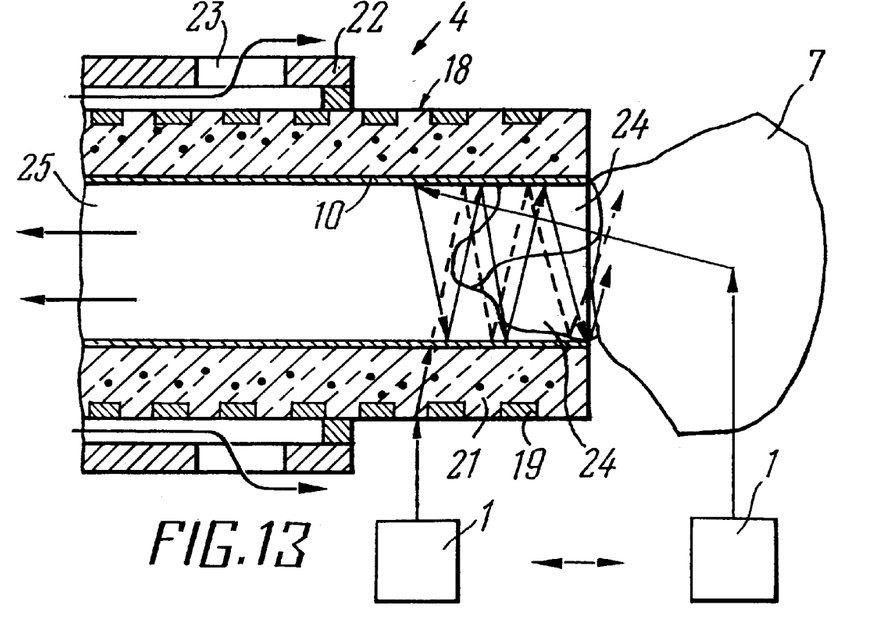
FIG. 13 shows the principle of operation of the device for removing a cataract, the intermediate stage of the surgical operation, in accordance with the invention.

Then the formed lens segments 24 are removed (FIG. 13). This stage begins with sucking one of the lens segments 24 to the input aperture of the aspiration channel 25, wherein the segment 24 partially enters the aspiration channel 25. The laser radiation is directed to the surface of a lens segment 24, but not to the end of the tube 21.

The laser radiation upon interaction with the substance of the lens 7 is converted into an acoustic wave (shown by the solid line with arrows in FIG. 13). The acoustic wave spreads in the anterior chamber 5 of the eye and gets into the hollow tube 21 where the means 10 for concentrating and the means 18 for converting are located. Multiple amplification of the acoustic wave takes place in the hollow tube 21 due to multiple reflection of the acoustic wave from the walls of the means 10 for concentrating. Then the amplified wave is directed to the surface of the lens 7, to a fragment 24 and cleaves it.

Further breaking up of the fragment 24 is effected by moving the laser tip 2 towards the tip 4 and positioning it above the surface of the tube 21. The laser radiation falls on the surface of the means 18 for converting and is transformed into acoustic oscillations which are transmitted to the inner surface of the tube to the means 10 for concentrating and are amplified by that means 10 a multiple number of times (shown in FIG. 13 by the dashed line). The amplified acoustic oscillations are directed to the surface of a fragment 24 at the aspiration aperture, causing further fragmentation of the lens substance which is at the aspiration channel 25, which results in final division of the fragment 24 of the lens 7 into small parts, the size of which is less than the diameter of the aspiration channel 25.

Figure 14:
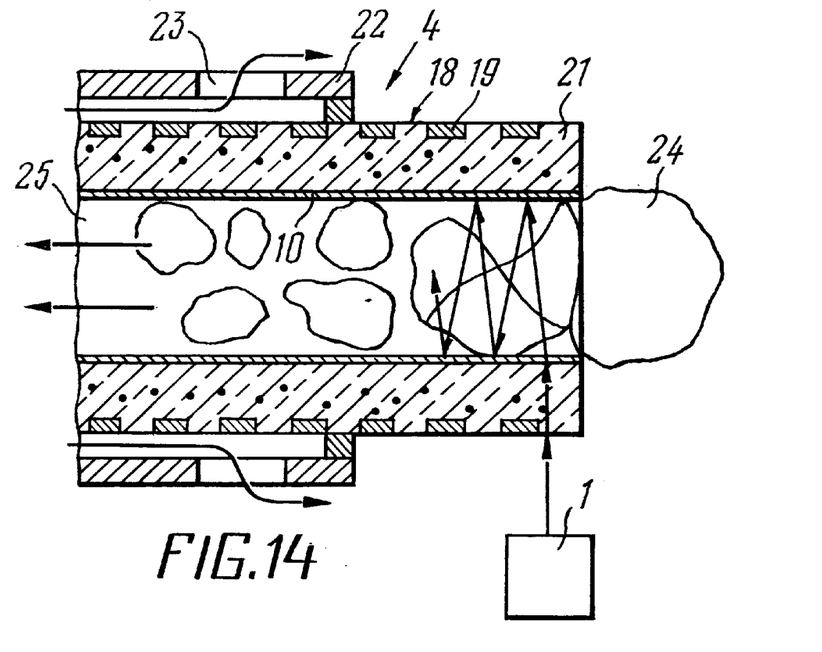
FIG. 14 shows the principle of operation of the device for removing a cataract, the final stage of the surgical operation, in accordance with the invention.

FIG. 14 shows the final stage of removal of pulverized lens fragments which enter the aspiration channel 25 during aspiration. In order to do this, the laser radiation is directed to the edge of the tube 21, where the radiation is absorbed by the material of the means 18 for converting and is transformed into additional acoustic oscillations. The latter are focused by the means 10 for concentrating onto a lens fragment 24 inside the tube 21 and further fragments the fragments 24, which makes it possible to effect their complete aspiration from the aspiration channel 25.

Figure 15:
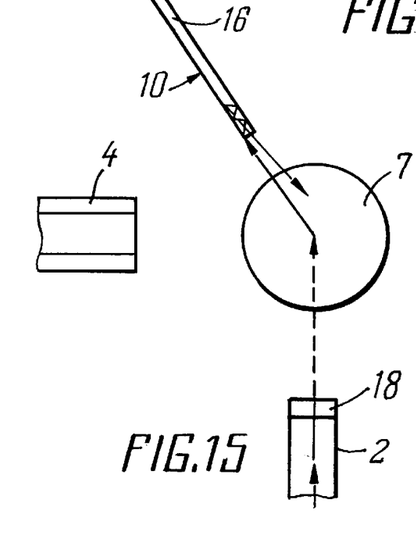
FIG. 15 shows an embodiment of execution of the device when the means for converting is placed on the laser tip and the means for concentrating is placed on an additional tip, in accordance with the invention.

If the means 10 (FIG. 15) for concentrating is placed on the additional tip 16, while the means 18 for converting is placed on the laser tip 2, a powerful amplification of the acoustic wave (shown by the dashed line) may be achieved with a fixed position of the laser tip 2, the irrigation-aspiration tip 4 and the additional tip 16 due to the effective conversion of laser radiation into an acoustic wave on the surface of the light guide, since there are no losses of laser energy caused by absorption of laser energy by a layer of water in front of the lens. Wherein the means 10 for concentrating amplifies the already amplified oscillations.

Figure 16:
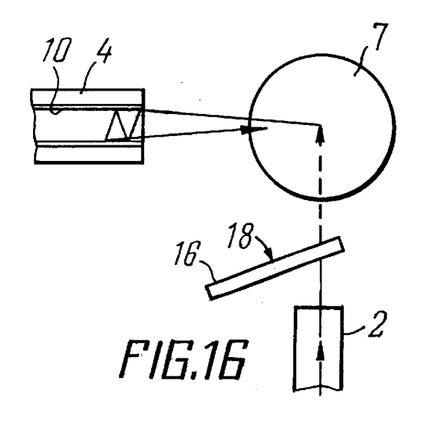
FIG. 16 shows an embodiment of the device when the means for converting is placed on an additional tip, and the means for concentrating is placed on the irrigation-aspiration tip, in accordance with the invention.

In the case where the means 10 (FIG. 16) for concentrating is placed on the irrigation-aspiration tip 4, while the means 18 for converting is placed on the additional tip 16, a powerful amplification of the acoustic wave (shown by the dashed line) may be achieved with a fixed position of the laser tip 2, irrigation-aspiration tip 4 and additional tip 16 due to the effective conversion of the laser radiation into the acoustic wave in direct proximity to the surface of the light guide, since losses of laser energy caused by absorption of laser energy by a layer of water in front of the lens are reduced, wherein the means 10 for concentrating amplifies the already amplified oscillations.

Figure 17:
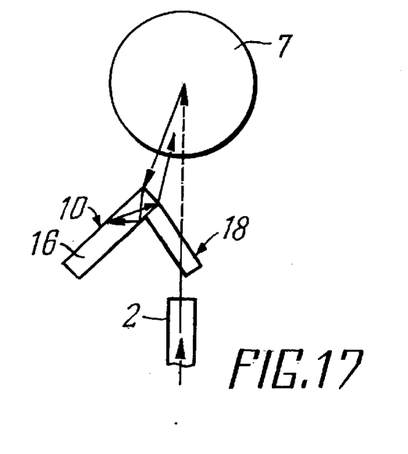
FIG. 17 shows an embodiment of the device when the means for converting and the means for concentrating are placed on an additional tip, in accordance with the invention.

In the case where the means 10 (FIG. 17) for concentrating and the means 18 for converting are placed on the additional tip 16, a powerful amplification of the acoustic wave (shown by the dashed line) may be achieved with a fixed position of the laser tip 2, irrigation-aspiration tip 4 and additional tip 16 due to the effective conversion of the laser radiation into the acoustic wave in direct proximity to the surface of the light guide, since losses of laser energy caused by absorption of laser energy by a layer of water in front of the lens are reduced.

Figure 18:
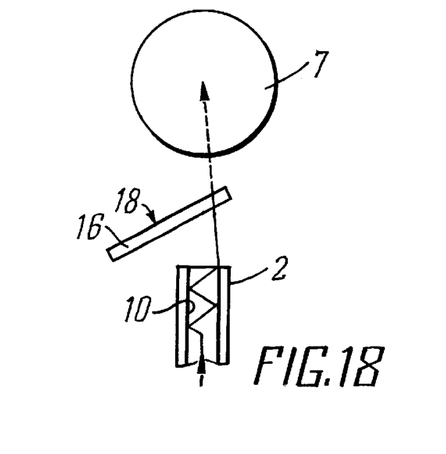
FIG. 18 shows an embodiment of the device when the means for concentrating is placed on the laser tip and the means for converting is placed on an additional tip which is located in the plane of propagation of the laser beam, in accordance with the invention.

In the case where the means 10 (FIG. 18) for concentrating is placed on the additional tip 16, while the means 18 for converting is placed on the laser tip 2, a powerful amplification of the acoustic wave (shown by the dashed line) may be achieved with a fixed position of the laser tip 2, irrigation-aspiration tip 4 and additional tip 16 due to the effective conversion of the laser radiation into the acoustic wave on the surface of the light guide, since there are no losses of laser energy caused by absorption of laser energy by a layer of water in front of the lens, and wherein the means 10 for concentrating amplifies the already amplified oscillations.

In the case where the means 10 (FIG. 5) for concentrating is placed on the additional tip 16 without the means 18 for converting, a powerful amplification of the acoustic wave may be achieved with a fixed position of the laser tip 2, irrigation-aspiration tip 4 and additional tip 16 due to the effective conversion of the laser radiation into the acoustic wave on the surface of the light guide, since there are no losses of laser energy caused by absorption of laser energy by a layer of water in front of the lens.

In order to prevent the sucking of the rear wall of the crystalline capsule towards the aspiration channel 25 while an operation is being carried out, the device comprises a means 26 (FIG. 1) for preventing the sucking which is made in the form of a scapula of polymeric material that is fixed to the working part of the irrigation-aspiration tip 4.

We claim:

1. A device for removing cataracts comprising
  a source of pulse laser radiation with a laser tip intended for insertion into the cavity of an eye through a first cut and having a working part intended for placement in the anterior section of the eye during removal of a cataract-changed lens,
  an irrigator/aspirator provided with a tip intended for insertion into the cavity of the eye through a second cut and having a working part intended for placement in the anterior section of the eye during removal of a cataract-changed lens,
  said laser tip is placed at an angle within the range of from 1 to 180 degrees relative to said irrigator/aspirator tip,
  a concentrator for concentrating on a cataract-changed lens of an eye or in direct proximity thereto an acoustic wave induced by pulse laser radiation from said source of pulse laser radiation impinging on the lens of an eye, the concentrator being made in the form of at least one hollow body, the walls of which are made of a material, whose light absorption factor at the wavelength of laser radiation is within the range of from 0.001 to 10 000 cm$^{-1}$ selected from the group consisting of fluorite, sapphire, quartz and phosphate glass, and the ratio of the length of which to its inner diameter is within the range of from 1 to 100, said concentrator placed coaxially with said irrigator/aspirator tip.

2. A device according to claim 1, wherein the concentrator comprises a hollow rod having a circular, elliptical or rectangular shape in cross section.

3. A device for removing cataracts according to claim 1, further comprising an additional tip which is placed in a third aperture in the anterior section of the eye during removal of a cataract-changed lens at an angle to the irrigator/aspirator tip which is within the range of from 1 to 180 degrees, and the concentrator placed in said additional tip.

4. A device according to claim 1, which comprises a converter for converting at least ¼ part of the laser radiation into an acoustic wave positioned in the path of the laser beam and made of a material, the light absorption factor of which at the wavelength of laser radiation is greater than the light absorption factor at the wavelength of laser radiation of said material of the concentrator, wherein the converter is in the form of a solid body or film or particles and is placed on a member selected from the group consisting of the laser tip, the irrigator-aspirator tip, an additional tip, and the concentrator, or in the body of the concentrator.

5. A device according to claim 4, wherein said converter is made of a material selected from the group consisting of silver, gold, platinum, aluminum, carbon, and titanium oxide.

6. A device according to claim 4, wherein a layer of material, the acoustic resistance of which is less than 100 Pa·s/m$^3$, is placed between said concentrator and said converter.

7. A device according to claim 1, wherein the wavelength of the source of laser radiation is within the range of from 1.06 to 2.94 micrometers.

8. A device according to claim 1, further comprising a modulator for converting the time structure of the laser pulse so that the modulation frequency of the laser pulse is equal to or a multiple of the resonance frequency of the means for concentrating the acoustic wave.

9. A device according to claim 1, wherein the roughness factor (Rz) of the inner surface of the irrigator-aspiration tip is less than 0.05.

10. A device for removing cataracts comprising a source of pulse laser radiation with a laser tip intended for insertion into the cavity of an eye through a first cut and having a working part intended for placement in the anterior section of the eye during removal of a cataract-changed lens, an irrigator/aspirator provided with a tip intended for insertion into the cavity of the eye through a second cut and having a working part intended for placement in the anterior section of the eye during removal of a cataract-changed lens, said laser tip is placed at an angle within the range of from 1 to 180 degrees relative to said irrigator/aspirator, a concentrator for concentrating on a cataract-changed lens of an eye or in direct proximity thereto an acoustic wave induced by pulse laser radiation from said source of pulse laser radiation impinging on the lens of an eye, the concentrator being made in the form of at least one hollow body, the walls of which are made of a material whose light absorption factor at the wavelength of laser radiation is within the range of from 0.001 to 10 000 cm$^{-1}$, and the ratio of the length of which to its inner diameter is within the range of from 1 to 100, said concentrator placed coaxially with said laser tip.

11. A device for removing cataracts comprising a source of pulse laser radiation with a laser tip intended for insertion into the cavity of an eye through a first cut and having a working part intended for placement in the anterior section of the eye during removal of a cataract-changed lens, an irrigator/aspirator for irrigation-aspiration provided with a tip intended for insertion into the cavity of the eye through a second cut and having a working part intended for placement in the anterior section of the eye during removal of a cataract-changed lens, said laser tip is placed at an angle within the range of from 1 to 180 degrees relative to said irrigator-aspirator tip, a concentrator for concentrating on a cataract-changed lens of an eye or in direct proximity thereto an acoustic wave induced by pulse laser radiation from said source of pulse laser radiation impinging on the lens of an eye, the concentrator being made in the form of at least one hollow body, the walls of which are made of a material whose light absorption factor at the wavelength of laser radiation is within the range of from 0.001 to 10 000 cm$^{-1}$, and the ratio of the length of which to its inner diameter is within the range of from 1 to 100, said concentrator placed coaxially with said irrigator-aspirator tip, means for preventing the sucking of the rear wall of the crystalline capsule towards the aspiration channel, the means for preventing the sucking being made in the form of a scapula of polymeric material and fixed to said working part of said irrigator-aspirator tip.

12. A device according to claim 11, wherein the irrigator-aspirator tip has an inner surface having a roughness factor (Rz) of less than 0.05.

* * * * *